US00PP31167P3

(12) United States Plant Patent
Schoone

(10) Patent No.: US PP31,167 P3
(45) Date of Patent: Dec. 3, 2019

(54) ***PHALAENOPSIS* PLANT NAMED 'CARROTCAKE'**

(50) Latin Name: *Phalaenopsis hybrida*
Varietal Denomination: Carrotcake

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 16/350,081

(22) Filed: Sep. 21, 2018

(65) Prior Publication Data

US 2019/0098821 P1 Mar. 28, 2019

Related U.S. Application Data

(60) Provisional application No. 62/561,904, filed on Sep. 22, 2017.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
See application file for complete search history.

*Primary Examiner* — Susan McCormick Ewoldt
(74) *Attorney, Agent, or Firm* — C. A. Whealy

(57) ABSTRACT

A new and distinct cultivar of *Phalaenopsis* plant named 'Carrotcake', characterized by its upright plant habit; moderately vigorous to vigorous growth habit; relatively short dark green-colored leaves; strong and relatively long flowering stems; freely flowering habit with typically at least two racemes per plant, each inflorescence with numerous flowers; and greyed orange-colored flowers with darker greyed orange-colored venation and red purple-colored labellum.

2 Drawing Sheets

Botanical designation: *Phalaenopsis hybrida.*
Cultivar denomination: 'CARROTCAKE'.

BACKGROUND OF THE INVENTION

The present invention relates to a new and distinct cultivar of *Phalaenopsis* plant, botanically known as *Phalaenopsis hybrida*, known by the breeder's reference 391135 and hereinafter referred to by the name 'Carrotcake'.

The new *Phalaenopsis* plant is a product of a planned breeding program conducted by the Inventor in Heemskerk, The Netherlands. The objective of the breeding program is to develop new rapid growing and freely flowering *Phalaenopsis* plants with good leaf shape and unique and attractive flower patterns and coloration.

The new *Phalaenopsis* plant originated from a cross-pollination in 2005 in Heemskerk, The Netherlands of *Phalaenopsis hybrida* 'Sin Yaun Golden Beauty', not patented, as the female, or seed, parent with *Phalaenopsis hybrida* 'Taisuco Date', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in 2013.

Asexual reproduction of the new *Phalaenopsis* plant by in vitro meristem propagation in a controlled environment in Heemskerk, The Netherlands since July, 2013 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Carrotcake'. These characteristics in combination distinguish 'Carrotcake' as a new and distinct *Phalaenopsis* plant:

1. Upright plant habit.
2. Moderately vigorous to vigorous growth habit.
3. Relatively short dark green-colored leaves.
4. Strong and relatively long flowering stems.
5. Freely flowering habit with typically at least two racemes per plant, each inflorescence with numerous flowers.
6. Greyed orange-colored flowers with darker greyed orange-colored venation and red purple-colored labellum.

Plants of the new *Phalaenopsis* can be compared to plants of the female parent, 'Sin Yaun Golden Beauty'. Plants of the new *Phalaenopsis* differ primarily from plants of 'Sin Yaun Golden Beauty' in the following characteristics:

1. Leaves of plants of the new *Phalaenopsis* are lighter green in color than leaves of plants of 'Sin Yaun Golden Beauty'.
2. Flowers of plants of the new *Phalaenopsis* are greyed orange in color whereas flowers of plants of 'Sin Yaun Golden Beauty' are yellow in color.

Plants of the new *Phalaenopsis* can be compared to plants of the male parent, 'Taisuco Date'. Plants of the new *Phalaenopsis* differ primarily from plants of 'Taisuco Date' in the following characteristics:

1. Flowers of plants of the new *Phalaenopsis* are more rounded in shape than and not as square as flowers of plants of 'Taisuco Date'.
2. Flowers of plants of the new *Phalaenopsis* have no spots whereas flowers of plants of 'Taisuco Date' have many spots.

Plants of the new *Phalaenopsis* can be compared to plants of *Phalaenopsis hybrida* 'Surf Song', not patented. In side-by-side comparisons, plants of the new *Phalaenopsis* differ primarily from plants of 'Surf Song' in flower size as flowers of the new *Phalaenopsis* are larger than flowers of plants of 'Surf Song'. In addition, leaves of plants of the new *Phalaenopsis* are more elongated than leaves of plants of 'Surf Song'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet is a side perspective view of a typical flowering plant of 'Carrotcake' grown in a container.

The photograph at the top of second sheet is a close-up view of a typical flower of 'Carrotcake'.

DETAILED BOTANICAL DESCRIPTION

The aforementioned photographs and following observations and measurements describe plants grown during the late summer in 10-cm containers in a glass-covered greenhouse in Heemskerk, The Netherlands and under cultural practices typically used in commercial *Phalaenopsis* production. During the production of the plants, day temperatures ranged from 20° C. to 22° C. and night temperatures averaged 18° C. and light levels ranged from 5 klux to 10 klux. Plants were three years old when the photographs and description were taken. In the following description, color references are made to The Royal Horticultural Society Colour Chart, 2015 Edition, except where general terms of ordinary dictionary significance are used.

Botanical classification: *Phalaenopsis hybrida* 'Carrotcake'.

Parentage:

*Female parent.*—*Phalaenopsis hybrida* 'Sin Yaun Golden Beauty', not patented.

*Male parent.*—*Phalaenopsis hybrida* 'Taisuco Date', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Fine, fibrous; typically light yellowish white in color, actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically at least two racemes per plant, each inflorescence with numerous flowers; monopodial; moderately vigorous to vigorous growth habit and moderate growth rate.

*Plant height, substrate level to top of foliar plane.*—About 13.8 cm.

*Plant height, substrate level to top of inflorescences.*—About 57 cm.

*Plant diameter or spread.*—About 32 cm.

Leaf description:

*Arrangement and quantity.*—Distichous, simple; sessile; about six per plant.

*Length.*—About 24 cm.

*Width.*—About 6.9 cm.

*Aspect.*—Mostly horizontal to slightly arching.

*Shape.*—Narrowly oblong to oblanceolate; moderately carinate.

*Apex.*—Acute, unequal.

*Base.*—Sheathing.

*Margin.*—Entire; slightly revolute.

*Texture and luster, upper surface.*—Smooth, glabrous; slightly glossy.

*Texture and luster, lower surface.*—Smooth, glabrous; moderately glossy.

*Venation pattern.*—Camptodromous.

*Color.*—Developing leaves, upper surface: Close to between NN137A and 147A. Developing leaves, lower surface: Close to 146A, strongly tinged with between N186C and 200A. Fully expanded leaves, upper surface: Close to NN137A; venation, close to NN137A. Fully expanded leaves, lower surface: Close to 146A; towards the margins, tinged with close to 147A; venation, close to 144A.

Inflorescence description:

*Appearance and flowering habit.*—Showy zygomorphic flowers arranged on axillary simple or branched racemes; typically at least two racemes per plant; each inflorescence with about nine open flowers; flowers face outwardly on arching inflorescences supported by upright peduncles; flowers with three petals, two lateral petals and one center petal transformed into a labellum and three sepals.

*Fragrance.*—None detected.

*Time to flower.*—Plants begin flowering about two months after flower bud initiation.

*Flower longevity.*—Long flowering period, individual flowers maintain good substance for about four to six months on the plant; flowers not persistent.

*Inflorescence length* (*lowermost flower to inflorescence apex*).—About 19.2 cm.

*Inflorescence width.*—About 12.3 cm.

*Flower buds.*—Height: About 1.8 cm. Diameter: About 1.2 cm. Shape: Ovate. Color: Close to N144A; tinged towards the apex with close to 175A.

*Flower diameter.*—About 7.9 cm by 8.6 cm.

*Flower depth.*—About 3 cm.

*Petals, quantity and arrangement.*—Three, two lateral petals and one center petal transformed into a labellum.

*Lateral petals.*—Length: About 4 cm. Width: About 4.3 cm. Shape: Reniform; slightly concave. Apex: Rounded. Margin: Entire. Texture and luster, upper surface: Smooth, glabrous, velvety; matte. Texture and luster, lower surface: Smooth, glabrous, velvety; slightly glossy. Color: When opening, upper surface: Close to 164C; fading towards the margins and apex to close to 154B; fine venation, close to 168A and 168B. When opening, lower surface: Close to 162A and 163C; central band, close to 154C; fading towards the margins and apex to close to 154B to 154C; fine venation, close to 164A. Fully opened, upper surface: Close to 163C; fading towards the apex to close to 154D; at the attachment point with the column, close to 186C to 186D; fine venation, close to 166B to 166C; color does not fade with development. Fully opened, lower surface: Close to 160A to 160B; fading towards the margins to close to 161B; fine venation, close to 164A and 164B; color does not fade with development.

*Labellum.*—Appearance: Tri-lobed with two lateral lobes and a central lobe. Length, lateral lobe: About 1.6 cm. Width, lateral lobes: About 8 mm. Length, central lobe: About 3.3 cm. Width, central lobe: About 1.4 cm. Shape, lateral lobes: Obovate. Shape, central lobe: Ovate to deltoid. Apex, lateral lobes: Obtuse. Apex, central lobe: Cleft with two moderately long recurved cirrose tips, about 9 mm in length and about 1.1 cm in width. Margins, lateral lobes: Entire. Margins, central lobe: Entire. Texture and luster, upper and lower surfaces: Smooth, glabrous, velvety; matte. Callosities: Located at the base of the labellum and attachment point of the lateral petals; about 4 mm in length, about 4 mm in width and about 3 mm in height. Color: When opening, upper surface: Lateral lobes: Close to 42B and 55B; fading towards the base to close to 4C; fine stripes and dots, close to 185A. Central lobe: Close to 179A; fading towards the apex to close to 185A; cirrose apices, close to 12B. Callosities: Close to 12C to 12D; fine dots, close to 185A. When opening, lower surface: Lateral lobes: Close to 180C and 180D; fading towards the margins and apex to close to 185A; towards the base, close to 2D. Central lobe: Close to 161C; fading towards the margins to close to N170B and N170C and at the edge, close to 171A; fading towards the apex to close to 4D; cirrose apices, close to 12C. Fully opened, upper surface: Lateral lobes: Close to between 72C to 72D and 180A; fading towards the base to close to 4D to lighter than 4D; fine stripes and dots, close to 187C. Central lobe: Close to 180A; fading towards the apex to close to 72C; cirrose apices, close to 179B. Callosities: Close to 17B to 17C; fine dots, close to 185A. Fully opened, lower surface: Lateral lobes: Close to 72D; fading towards the margins and apex to close to 179A and 179B; towards the base, close to 156D. Central lobe: Close to 77C; fading towards the margins to close to between N170B and 172A and at the edge, close to 4D; fading towards the base to close to 76B; cirrose apices, close to 77C.

*Sepals.*—Quantity and arrangement: Three, two lower lateral sepals and one upper dorsal sepal. Length, lateral sepal: About 4.1 cm. Width, lateral sepals: About 2.7 cm. Length, dorsal sepal: About 4 cm. Width, dorsal sepal: About 3.1 cm. Shape, lateral sepals: Ovate. Shape, dorsal sepal: Obovate to broadly elliptic. Apex, lateral and dorsal sepals: Obtuse. Base, lateral and dorsal sepals: Truncate. Margin, lateral and dorsal sepals: Entire. Texture and luster, lateral and dorsal sepals, upper and lower surfaces: Smooth, glabrous, velvety; matte. Color: When opening, upper surface: Lateral sepals: Close to 163C; fading towards the base, margins and apex to close to 154B; fine venation, close to N170A. Dorsal sepals: Close to 164C; fading towards the margins and apex to close to 154B; fine venation, close to N170A. When opening, lower surface: Lateral sepals: Close to between 153D and 154C; slightly fading towards the margins and apex to close to N170B. Dorsal sepals: Close to 162A and 163C; central band, close to 154C; fading towards the margins and apex to close to 154B to 154C; fine venation at the margins, close to 164A. Fully opened, upper surface: Lateral sepals: Close to 160A; fading towards the base, margins and apex to close to 154B; at the attachment point with the column, close to 186C to 186D; fine venation, close to 172A and 172B; color does not fade with development. Dorsal sepals: Close to 164C; fading towards the margins and apex to close to 154B; at the base, close to 186C to 186D; fine venation, close to 172A; color does not fade with development. Fully opened, lower surface: Lateral sepals: Close to between 153D and 154C; slightly veined at the margins and apex, close to N170A to N170B; color does not fade with development. Dorsal sepals: Close to 162A and 163C; central band, close to 154C; fading towards the margins and apex to close to 154B to 154C; fine venation at the margins, close to 164A; color does not fade with development.

*Peduncles.*—Length: About 54.6 cm. Diameter: About 5.5 mm. Strength: Very strong. Aspect: Upright to about 30° from vertical. Texture and luster: Smooth, glabrous; matte. Color: Close to 148A with fine dots, close to 144B.

*Pedicels.*—Length: About 4 cm. Diameter: About 3 mm. Strength: Moderately strong. Aspect: About 45° from peduncle axis. Texture and luster: Smooth, glabrous; matte. Color: Close to 145A; distally, fading to close to 150D.

*Reproductive organs.*—Androecium: Column length: About 1 cm. Column width: About 6 mm. Column color: Upper surface, close to 75B; lower surface, close to N75A. Pollinia quantity: Two. Pollinia diameter (per two pollinia): About 2.5 mm. Pollinia color: Close to 23B. Gynoecium: Stigma length: About 3 mm. Stigma width: About 3 mm. Stigma shape: Reniform. Stigma color: Close to NN155B. Ovary length: About 1.2 cm. Ovary diameter: About 1 mm. Ovary color: Close to lighter than 150D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 10° C. to about 40° C. and to be suitable for USDA Hardiness Zone 10.

It is claimed:

1. A new and distinct *Phalaenopsis* plant named 'Carrotcake' as illustrated and described.

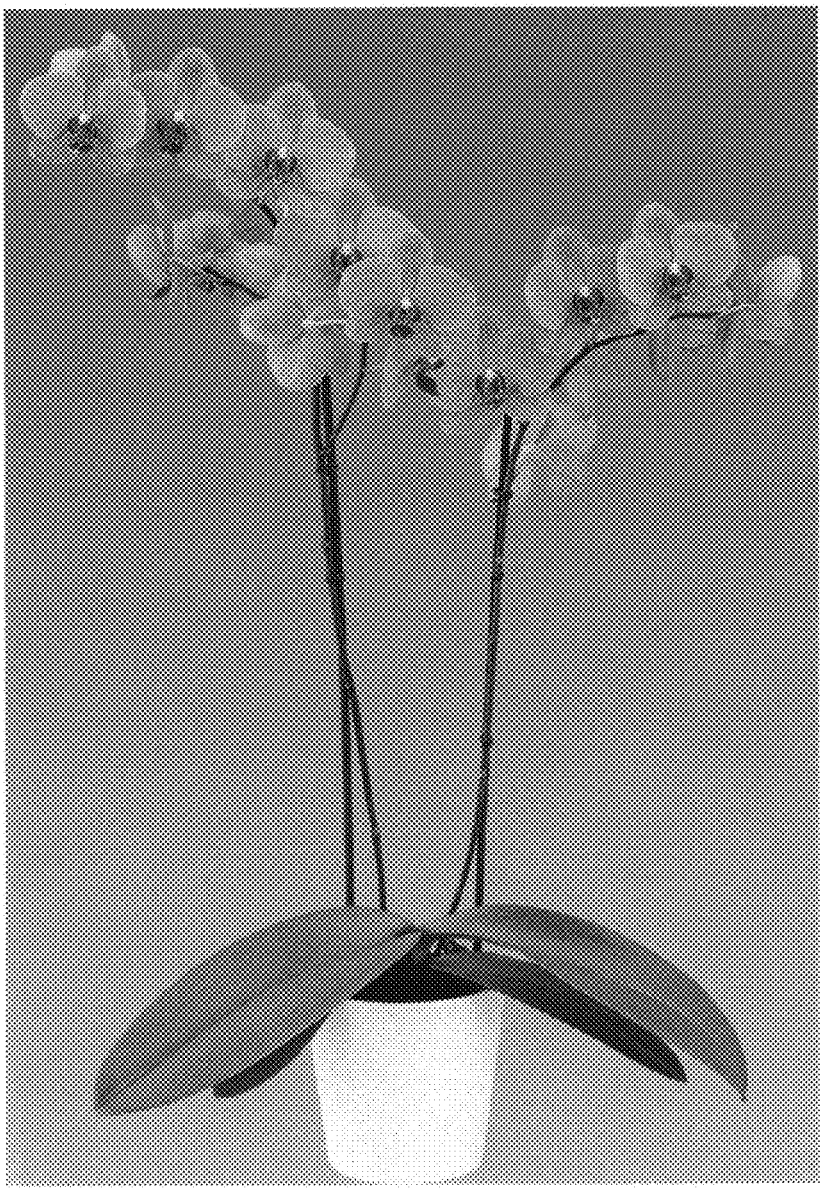

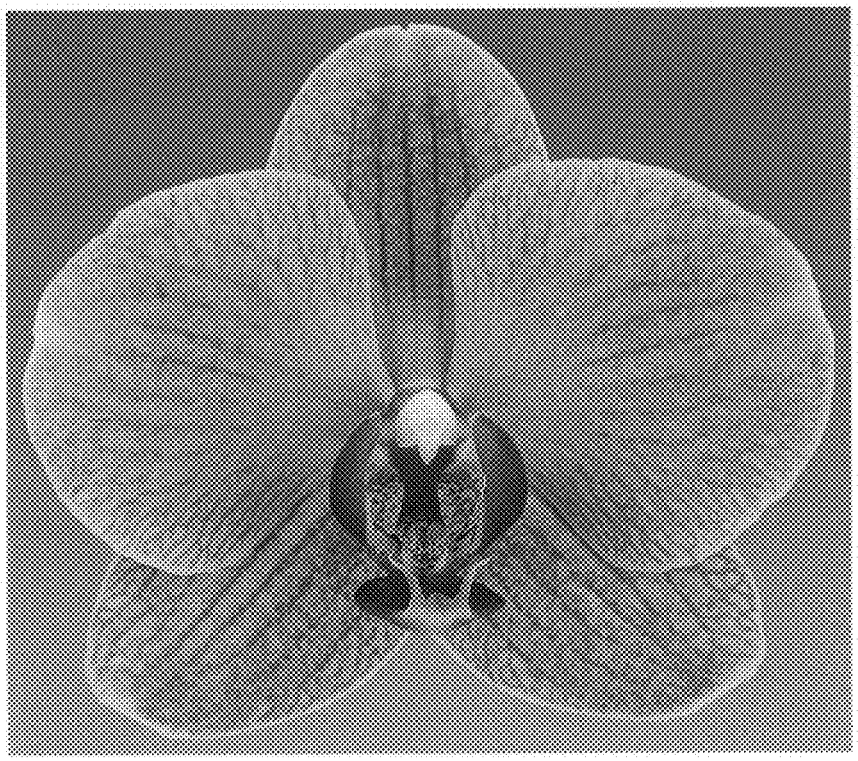

* * * * *